US012667323B2

(12) United States Patent
Kano et al.

(10) Patent No.: US 12,667,323 B2
(45) Date of Patent: Jun. 30, 2026

(54) MEDICAL INFORMATION PROCESSING APPARATUS, MEDICAL INFORMATION PROCESSING METHOD, AND RECORDING MEDIUM

(71) Applicant: Canon Kabushiki Kaisha, Tokyo (JP)

(72) Inventors: Yusuke Kano, Nasushiobara (JP); Sho Sasaki, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 635 days.

(21) Appl. No.: 17/936,495

(22) Filed: Sep. 29, 2022

(65) Prior Publication Data

US 2023/0101650 A1 Mar. 30, 2023

(30) Foreign Application Priority Data

Sep. 30, 2021 (JP) ................................. 2021-160723

(51) Int. Cl.
*A61B 6/00* (2024.01)
*G06N 7/01* (2023.01)

(52) U.S. Cl.
CPC ............. *A61B 6/5217* (2013.01); *G06N 7/01* (2023.01)

(58) Field of Classification Search
CPC ................... A61B 6/5217; G06N 7/01; G06Q 50/20–26
See application file for complete search history.

(56) References Cited

U.S. PATENT DOCUMENTS

2007/0269804 A1* 11/2007 Liew ...................... G16B 40/00
                                                    702/19
2015/0190098 A1 7/2015 Patek et al.
2024/0006080 A1* 1/2024 Molero Leon ......... G16H 10/60

FOREIGN PATENT DOCUMENTS

WO     WO 2021/065845 A1     4/2021

OTHER PUBLICATIONS

F. V. Jensen. "Bayesian Networks and Decision Graphs". Springer. (Year: 2001).*
Guo et al., Forward Stagewise Shrinkage and Addition for High Dimensional Censored Regression, 7(2) Stat Bioscience 225-244 (Oct. 1, 2015) (Year: 2015).*
Sanchez-Pinto et al., Comparison of variable selection methods for clinical predictive modeling, 116 Int J of Medical Informatics 10-17 (Year: 2018).*
Lu et al., Bandit Algorithms for Precision Medicine, University of Michigan Dept of Statistics (Aug. 11, 2021) (Year: 2021).*
Hoffman et al., On correlation and budget constraints in model-based bandit optimization with application to automatic machine learning, Proceedings of the Seventeenth International Conference on Artificial Intelligence and Statistics 365-374 (Year: 2014).*

(Continued)

*Primary Examiner* — Jordan L Jackson
(74) *Attorney, Agent, or Firm* — Oblon, McClelland, Maier & Neustadt, L.L.P.

(57) ABSTRACT

According to one embodiment, a medical information processing apparatus includes processing circuitry which updates a model for calculating an effect evaluation value for a medical decision. The processing circuitry updates a parameter of the model while retaining the structure of the model so that the structure of the model is updated less frequently than the parameter.

19 Claims, 10 Drawing Sheets

(56) References Cited

OTHER PUBLICATIONS

Yasui, S., "Bandit and Casual Inference", CMFL Study Session, https://speakerdeck.com/housecat442/bandeitutotoyin-quio-tui-1un?slide=38>, 2019, 2 pages.

Hernán, M. et al., "A Second Chance to Get Causal Inference Right: A Classification of Data Science Tasks", Chance, vol. 32.1, 2019, 9 pages.

Subbaswamy, A. et al., "From Development to Deployment: Dataset Shift, Causality, and Shift-Stable Models in Health AI", Biostatistics, 21(2), 2020, 8 pages.

Schroeder, T., "Evidence-Based Medicine in Rapidly Changing Technologies", Scandinavian Journal of Surgery, 97(2), 2008, 6 pages.

Bergvist, D. et al, "Randomized Trials or Population-Based Registries", European Journal of Vascular and Endovascular Surgery, 34(3), 2007, 4 pages.

Schork, N., "Randomized Clinical Trials and Personalized Medicine", Social Science & Medicine, 210, 71-73, 2018, 7 pages.

Angus, D. et al, "Adaptive Platform Trials: Definition, Design, Conduct and Reporting Considerations", Social Science & Medicine, Nature Reviews Drug Discovery, 18(6), 2019, 12 pages.

Extended European Search Report issued on Feb. 15, 2023 in European Patent Application 22198867.8, 8 pages.

\* cited by examiner

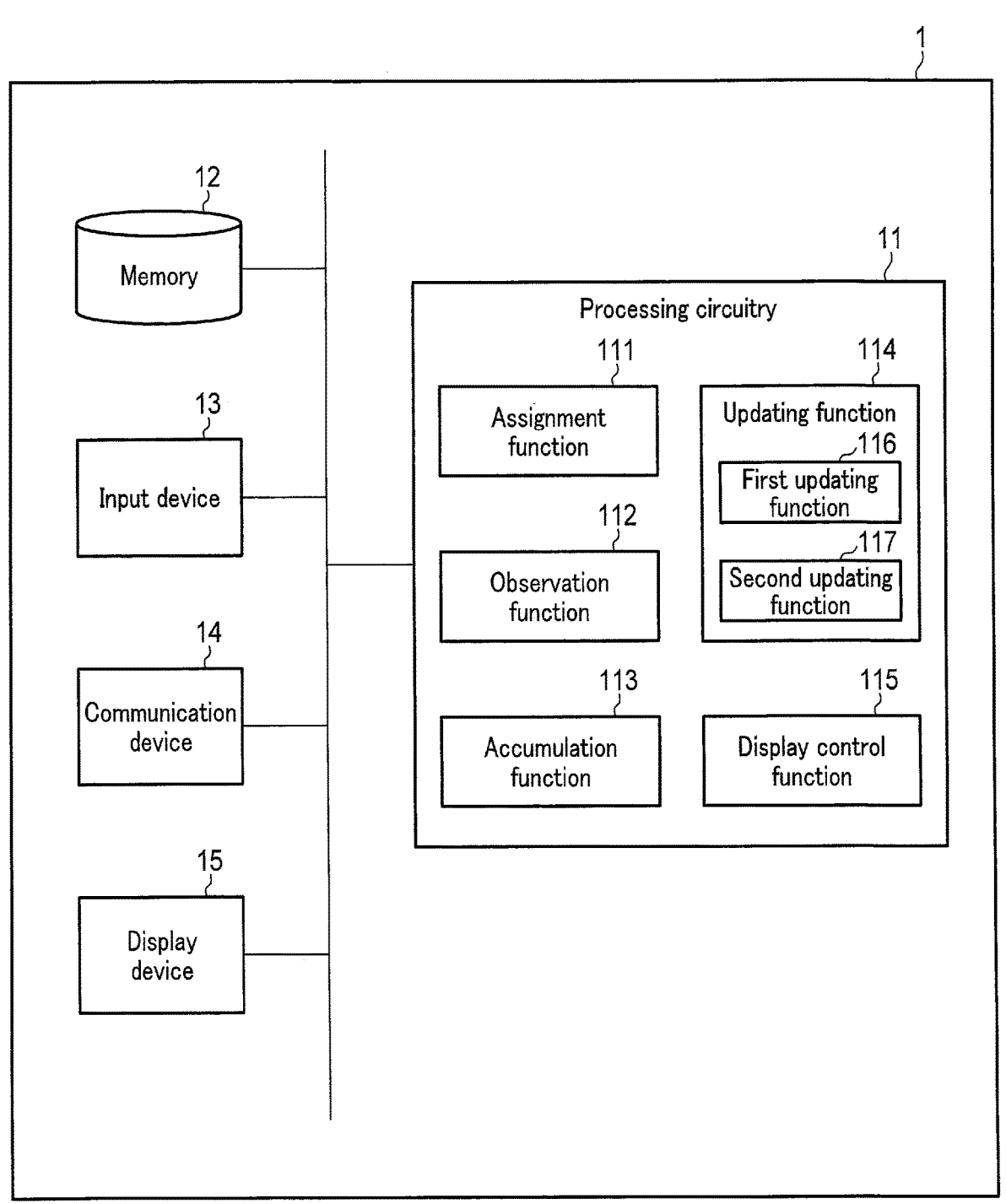
F I G. 1

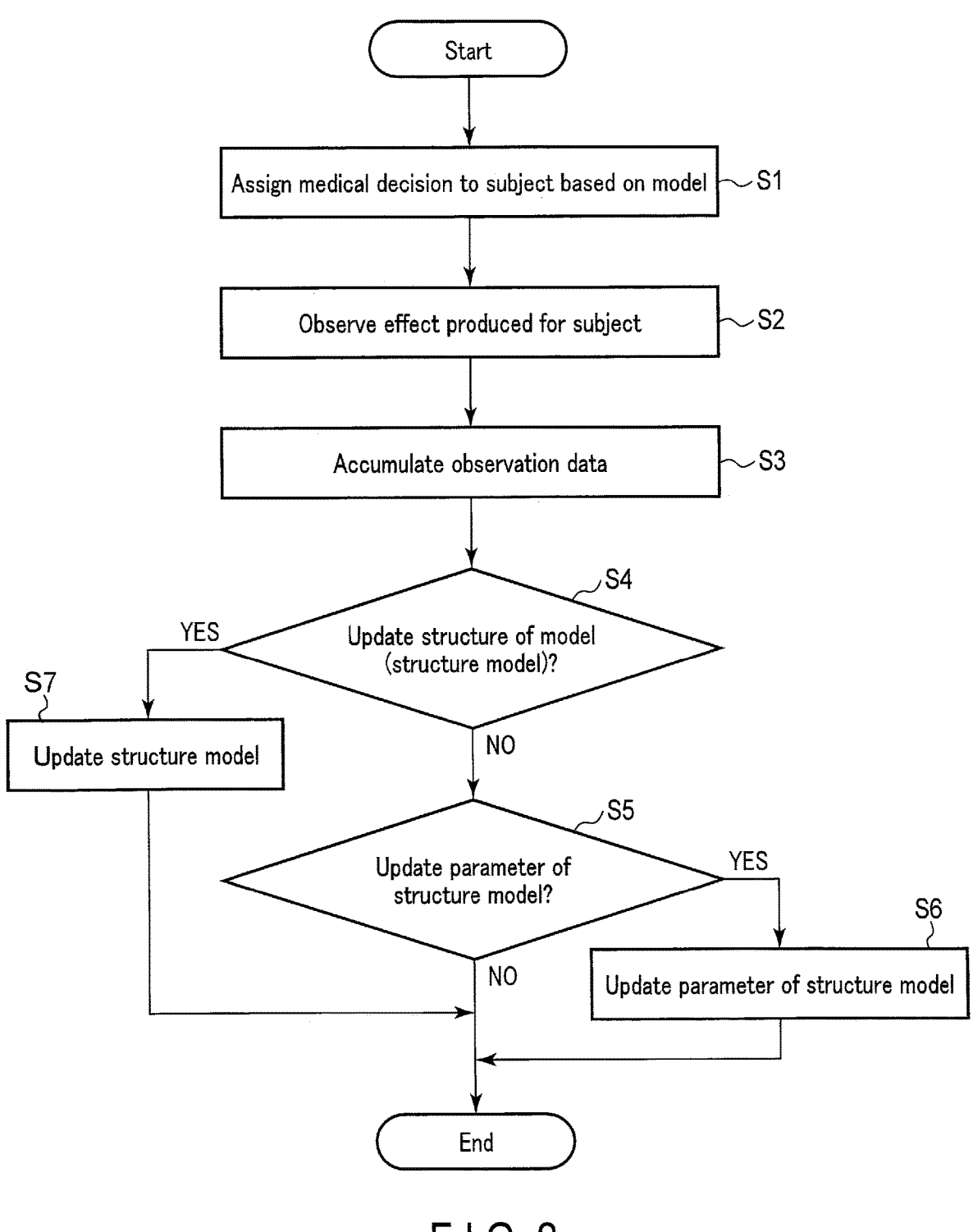
F I G. 2

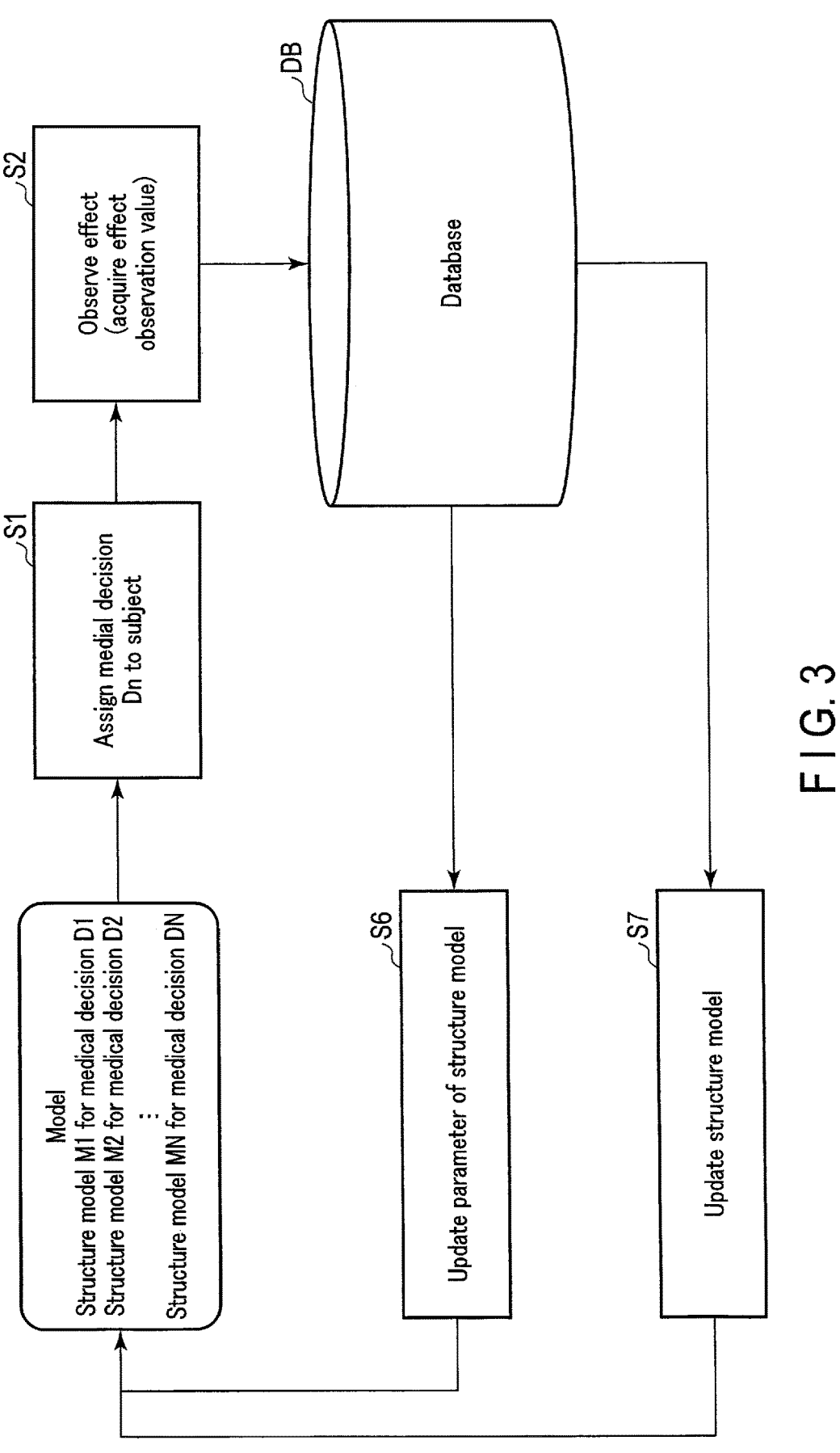
F I G. 3

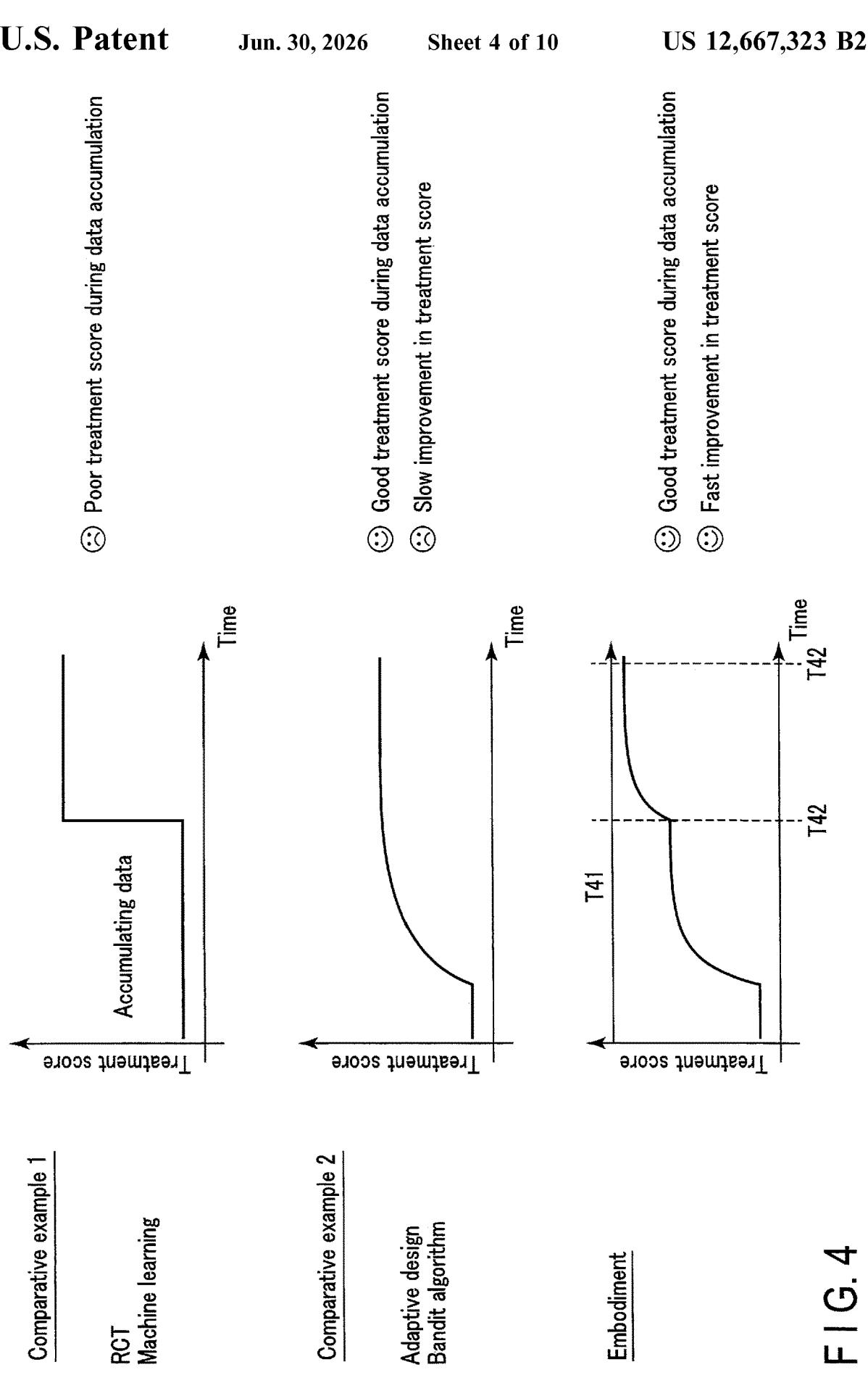
F I G. 4

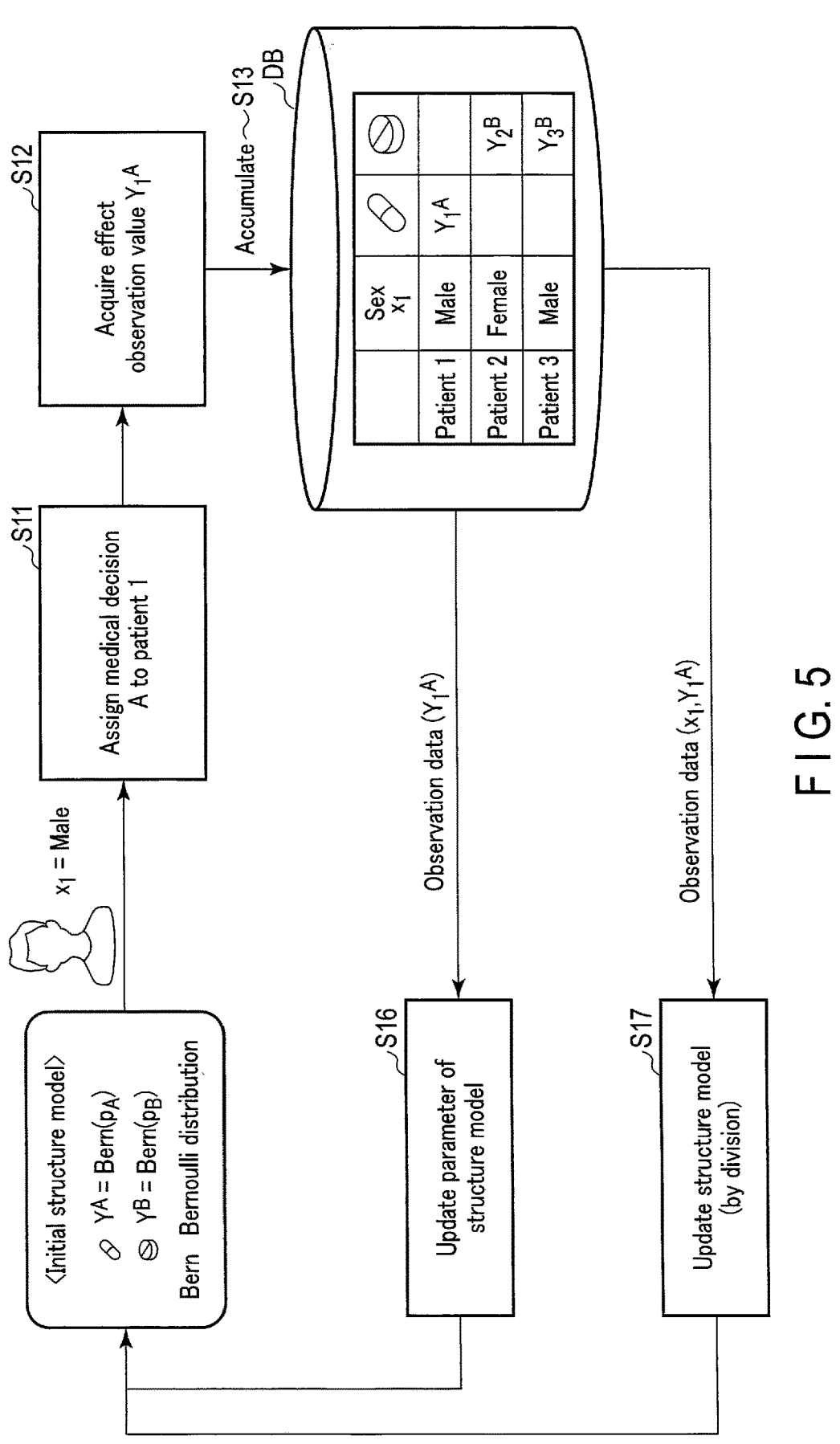
F I G. 5

| | Parameter |
|---|---|
| Structure model for medical decision A for male | $\alpha_{A,M}, \beta_{A,M}$ |
| Structure model for medical decision A for female | $\alpha_{A,F}, \beta_{A,F}$ |
| Structure model for medical decision B for male | $\alpha_{B,M}, \beta_{B,M}$ |
| Structure model for medical decision B for female | $\alpha_{B,F}, \beta_{B,F}$ |

Division

| | Parameter |
|---|---|
| Structure model for medical decision A | $\alpha_A, \beta_A$ |
| Structure model for medical decision B | $\alpha_B, \beta_B$ |

F I G. 6

| | Parameter |
|---|---|
| Structure model for medical decision A | $\alpha_A, \beta_A$ |
| Structure model for medical decision B | $\alpha_B, \beta_B$ |

Combining

| | Parameter |
|---|---|
| Structure model for medical decision A for male | $\alpha_{A,M}, \beta_{A,M}$ |
| Structure model for medical decision A for female | $\alpha_{A,F}, \beta_{A,F}$ |
| Structure model for medical decision B for male | $\alpha_{B,M}, \beta_{B,M}$ |
| Structure model for medical decision B for female | $\alpha_{B,F}, \beta_{B,F}$ |

FIG.7

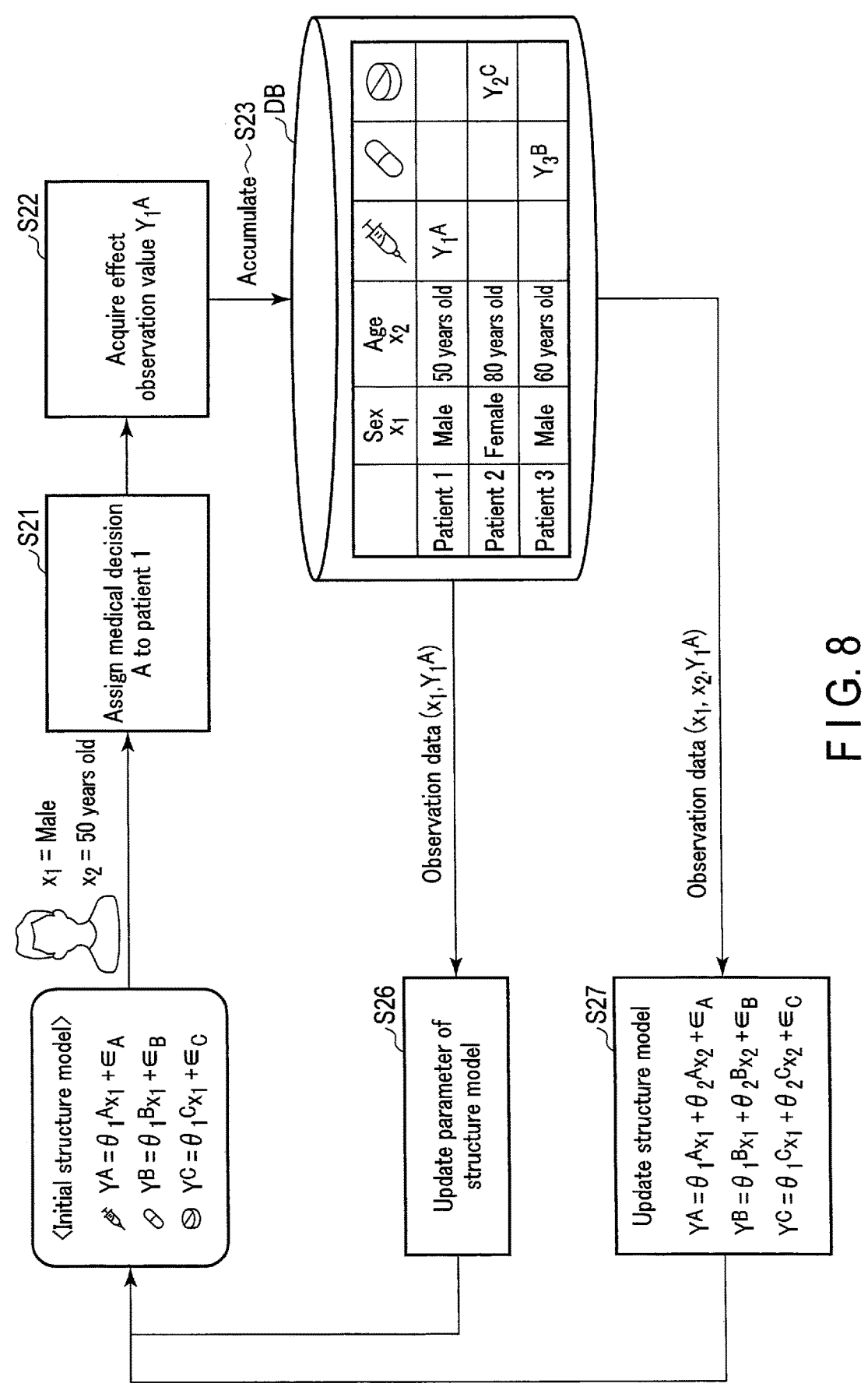
F I G. 8

$$Y^A = \theta_1^A x_1 + \in_A$$

$$Y^B = \theta_1^B x_1 + \in_B$$

$$Y^C = \theta_1^C x_1 + \in_C$$

Add feature amount $x_2$

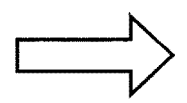

$$Y^A = \theta_1^A x_1 + \theta_2^A x_2 + \in_A$$

$$Y^B = \theta_1^B x_1 + \theta_2^B x_2 + \in_B$$

$$Y^C = \theta_1^C x_1 + \theta_2^C x_2 + \in_C$$

F I G. 9

$$Y^A = \theta_1^A x_1 + \theta_2^A x_2 + \in_A$$

$$Y^B = \theta_1^B x_1 + \theta_2^B x_2 + \in_B$$

$$Y^C = \theta_1^C x_1 + \theta_2^C x_2 + \in_C$$

Delete
feature amount $x_2$

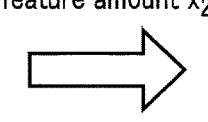

$$Y^A = \theta_1^A x_1 + \in_A$$

$$Y^B = \theta_1^B x_1 + \in_B$$

$$Y^C = \theta_1^C x_1 + \in_C$$

F I G. 10

$$Y^A = \theta_1^A x_1 + \in_A$$

$$Y^B = \theta_1^B x_1 + \in_B$$

$$Y^C = \theta_1^C x_1 + \in_C$$

Replace
feature amount $x_1$

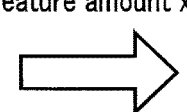

$$Y^A = \theta_2^A x_2 + \in_A$$

$$Y^B = \theta_2^B x_2 + \in_B$$

$$Y^C = \theta_2^C x_2 + \in_C$$

F I G. 11

$$Y^A = \theta_1{}^A x_1 + \in_A$$
$$Y^B = \theta_1{}^B x_1 + \in_B$$
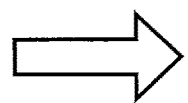
Add medical decision C
$$Y^A = \theta_1{}^A x_1 + \in_A$$
$$Y^B = \theta_1{}^B x_1 + \in_B$$
$$Y^C = \theta_1{}^C x_1 + \in_C$$
F I G. 12
$$Y^A = \theta_1{}^A x_1 + \in_A$$
$$Y^B = \theta_1{}^B x_1 + \in_B$$
$$Y^C = \theta_1{}^C x_1 + \in_C$$
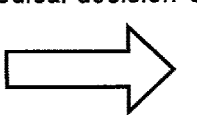
Abolish
medical decision C
$$Y^A = \theta_1{}^A x_1 + \in_A$$
$$Y^B = \theta_1{}^B x_1 + \in_B$$
F I G. 13

MEDICAL INFORMATION PROCESSING APPARATUS, MEDICAL INFORMATION PROCESSING METHOD, AND RECORDING MEDIUM

CROSS-REFERENCE TO RELATED APPLICATION(S)

This application is based upon and claims the benefit of priority from Japanese Patent Application No. 2021-160723, filed Sep. 30, 2021, the entire contents of which are incorporated herein by reference.

FIELD

Embodiments described herein relate generally to a medical information processing apparatus, a medical information processing method, and a recording medium.

BACKGROUND

Assigning a given medical decision from a number of medical decisions to a patient is practiced in clinical researches and daily medical treatment. Adaptive design, bandit algorithms, etc. are known techniques to adaptively tailor such assignments. Models according to these techniques can refine medical decisions even during data accumulation, unlike supervised learning or the like. However, sophisticating the models could delay the refinement of medical decisions, and simplifying the models could degrade the inference accuracy. As such, adjustment of the models may pose a trade-off of lowering the degree of realizable refinement of medical decisions.

BRIEF DESCRIPTION OF THE DRAWINGS

FIG. 1 is a diagram showing an exemplary configuration of a medical information processing apparatus according to an embodiment.

FIG. 2 is a flowchart showing medical information processing that is conducted by processing circuitry in accordance with a medical information processing program.

FIG. 3 is a diagram schematically illustrating the medical information processing shown in FIG. 2.

FIG. 4 is a diagram showing transitions of treatment scores of techniques according to the embodiment, Comparative Example 1, and Comparative Example 2.

FIG. 5 is a diagram schematically illustrating medical information processing according to Working Example 1.

FIG. 6 is a diagram showing exemplary structure models and their parameters before and after division.

FIG. 7 is a diagram showing exemplary structure models and their parameters before and after combining.

FIG. 8 is a diagram schematically illustrating medical information processing according to Working Example 2.

FIG. 9 is a diagram showing exemplary structure models before and after addition of a feature amount $x_2$.

FIG. 10 is a diagram showing exemplary structure models before and after deletion of a feature amount $x_2$.

FIG. 11 is a diagram showing exemplary structure models before and after replacement of a feature amount $x_1$ with a feature amount $x_2$.

FIG. 12 is a diagram showing exemplary structure models before and after addition of medical decision C.

FIG. 13 is a diagram showing exemplary structure models before and after abolition of medical decision C.

DETAILED DESCRIPTION

According to one embodiment, a medical information processing apparatus includes processing circuitry adapted to update a model for calculating an effect evaluation value for a medical decision. The processing circuitry updates a parameter of the model while retaining the structure of the model so that the structure of the model is updated less frequently than the parameter.

Embodiments of a medical information processing apparatus, a medical information processing method, and a recording medium will be described in detail with reference to the drawings.

In the medical field, efforts to realize clinical decision support (CDS) using technologies based on data and artificial intelligence (AI) are ongoing. In general, AI technologies employ supervised learning as represented by deep learning, and some of these techniques are beginning to have a lesion detecting capacity outrunning, in especially the image diagnosis domain, the accuracy of a human being.

However, the following circumstances are expected to hinder the realization of clinical decision support (CDS) through supervised learning. First, improvement in accuracy requires an enormous amount of data, which would incur large costs for data collection. Second, despite the related high accuracy, a proper clinical decision may not result.

The second issue is technically synonymous with a problem that supervised learning, while being capable of revealing a correlation, cannot demonstrate a causal sequence. For example, even if an AI model can predict the within-5-year death of a heart failure patient with 100% accuracy, such an AI model cannot assist a doctor who wants to know the method for extending the remaining life of this patient to 5 years or longer.

Demonstrating a causal sequence in medical activities to thereby specify the best medical option is yet to be realized by the supervised learning of the day, and this is a role of randomized controlled trials (RCT) or medical statistics. In other words, as long as the current AI technologies prevail, a clinical decision support (CDS) for the optimized treatment cannot be realized in the true sense, and randomized controlled trials (RCT) will not disappear.

Randomized controlled trials (RCT) also involve many problems. For example, these problems include, first, the significant amount of time required to complete the research, which makes it impossible to follow the latest trends, thus the resultant findings could easily become obsolete. Second, the research is very costly, which is also accompanied by a risk of failure to prove the hypothesis, thus efficiency is not guaranteed. Third, in general, eligibility criteria set for the research are strict, which could render the resultant findings inapplicable for ordinary patients (i.e., result in low external validity). Fourth, as a control, only an average intervention effect can be employed, which does not allow for effects that vary among individual patients to be specified. For example, cases such as personalized medicine cannot be assumed. Fifth, statistical significance could be overly relied upon, which may easily lead to publication bias, p-hacking, etc.

In particular, currently, treatment methodologies are frequently updated and renewed, which together raise the importance of personalized medicine. Thus, the limits of randomized controlled trials (RCT) are becoming apparent.

Accordingly, there is a demand for efficient optimization of medical decisions that does not require a large amount of data in advance and that can be performed without randomized controlled trials (RCT). Furthermore, for this purpose, formulation of models for clinical decision support (CDS) is desired.

FIG. 1 is a diagram showing an exemplary configuration of a medical information processing apparatus 1 according to an embodiment. As shown in FIG. 1, the medical information processing apparatus 1 is an information processing terminal which may be a computer, etc., including processing circuitry 11, a memory 12, an input device 13, a communication device 14, and a display device 15. The processing circuitry 11, the memory 12, the input device 13, the communication device 14, and the display device 15 are connected with one another via a bus so that they can mutually input and output signals.

The processing circuitry 11 includes one or more processors such as a central processing unit (CPU), a graphics processing unit (GPU), and so on. The processing circuitry 11, by running one or more medical information processing programs, implements various functions, including an assignment function ill, an observation function 112, an accumulation function 113, an updating function 114, and a display control function 115. Note that the functions 111 to 115 are not limited to the implementation through a single processing circuitry component. Multiple independent processors may be employed together to form processing circuitry so that the respective processors run the programs to realize the functions 111 to 115. Moreover, the functions 111 to 115 may be respective programs serving as modules to constitute a medical information processing program. Such programs may be stored in the memory 12.

The memory 12 is a storage device adapted to store various types of information sets, such as one or any combination of a read only memory (ROM), a random access memory (RAM), a hard disk drive (HDD), a solid state drive (SSD), an integrated circuit memory device, and so on. Other than such storage devices, the memory 12 may be one or any combination of non-transitory computer-readable recording media such as a compact disc (CD), a digital versatile disc (DVD), and a flash memory, or a driver that reads and writes various types of information sets with semiconductor memory devices. Also, the memory 12 may be located within an external computer connected via a network.

The input device 13 receives various input operations from an operator and converts the received input operations into electrical signals for output to the processing circuitry 11. More specifically, the input device 13 is coupled to one or more input instruments such as a mouse, a keyboard, a track ball, switches, buttons, a joystick, a touch pad, and a touch panel display. The input device 13 outputs electric signals corresponding to input operations received by such input instruments to the processing circuitry 11. Note that the input device 13 may be furnished at an external computer connected via a network, etc.

The communication device 14 is an interface for exchanging various types of information sets with one or more external computers. The communication device 14 performs data communication according to the standard suitable for medical information communication, such as a digital imaging and communications in medicine (DICOM).

The display device 15 displays various types of information sets according to the display control function 115 of the processing circuitry 11. The display device 15, for example, may be a liquid crystal display (LCD), a cathode ray tube (CRT) display, an organic electroluminescence display (OELD), a plasma display, or any other display available. The display device 15 may instead be a projector.

The processing circuitry 11 according to the embodiment, with the assignment function 111, determines a medical decision to be assigned to a subject such as a patient, based on an effect evaluation value for the medical decision. Such effect evaluation values for medical decisions are calculated using models adapted to calculate the effect evaluation values for medical decisions. The subject receives a medical act corresponding to the assigned medical decision. An effect attributable to the medical act is produced for the subject. The processing circuitry 11, with the observation function 112, observes the effect produced for the subject. The effect is represented by a numerical value. This numerical value will be called an "effect observation value". With the accumulation function 113, the processing circuitry 11 accumulates observation data, in which the effect observation value, the medical act, and other feature amount or amounts are associated with each other, in the memory 12. Such assignment of a medical decision, observation of an effect, and accumulation of observation data are conducted for various subjects. With the updating function 114, the processing circuitry 11 individually and sequentially updates, during the accumulation of observation data, parameters and structures of models based on the observation data. With the display control function 115, the processing circuitry 11 presents various data sets through the display device 15.

The updating function 114 may be divided into a first updating function 116 and a second updating function 117. With the first updating function 116, the processing circuitry 11 updates a parameter of a model while retaining the structure of the model. With the second updating function 117, the processing circuitry 11 updates the structure of the model at a frequency lower than that for updating the parameter.

The subject in the context of the present embodiment is typically a single patient suffering from a disease. However, the subject assumed by the embodiment is not limited to this but may be a patient group constituted by two or more patients. Also, the subject in the embodiment is not limited to a person suffering from a disease, but may be a healthy person. The models may be employed for respective doctors, respective treatment departments, respective hospitals, or respective geographical areas. The models may also be employed for respective subjects.

Each model according to the embodiment is a function for calculating the effect evaluation value for a medical decision. This function may be a function defined by a manual operation, a function defined by an experimental approach or a deterministic approach, a function formed through training in machine learning, or a function defined by any other methods. The effect evaluation value is an index value for evaluating the effect of an assignment candidate medical decision, and examples of such an index value include a confidence interval of the effect, an expected value of the effect, the highest value among such expected values, a difference from the highest expected value, and so on.

The embodiment assumes types of medical decisions including execution/non-execution-related decisions, content-related decisions, amount-related decisions, and time-related decisions. Examples of the execution/non-execution-related decisions include a decision as to whether or not to execute a surgery or whether or not to execute a blood test. Examples of the content-related decisions include a decision for the selection of a drug to be used or the selection of a disease name to which diagnosis is conducted. Examples of the amount-related decisions include a decision for the selection of a dose of pharmaceuticals or the selection of a rehabilitation duration. Examples of the time-related decisions include a decision for the selection of a time to visit a hospital or the selection of a time to execute a surgery.

Persons who make medical decisions are not limited to medical professionals such as doctors, nurses, and other health-care providers, but may include subjects themselves, family members of subjects, and any other persons associated with subjects. Medical decisions are not always required to be advanced or sophisticated decisions for healthcare, nor are they limited to the purposes of health improvement. That is, medical decisions may cover decisions that lead to a worse result for medicine, health, etc. For example, a decision as to whether or not a healthy individual smokes a cigarette at a given timing is also assumed to be a medical decision.

A medical decision consequently results in a certain effect. Such an effect is called a "reward" or an "outcome". Effects discussed in the context of the embodiment are assumed to be, for example, clinical outcomes, patient-reported outcomes, and economic outcomes. Examples of the clinical outcomes include a morbidity rate (including whether or not a subject suffers from a disease or the like), a 5-year survival rate (including whether or not a subject is alive), a complication incidence rate (including whether or not a subject suffers from complications), a re-hospitalization rate (including whether or not a subject is hospitalized again), test values or an improvement degree of test values, and an independence degree in daily life. Examples of the patient-reported outcomes include a subjective symptom, a subjective health condition, a satisfaction level of treatment, and a subjective level of happiness. Examples of the economic outcomes include medical costs, invested medical resources, and a length of stay at a hospital.

The effects may be given as numerical representations, to which a superiority-and-inferiority assessment can be done for learning. Numerical values may be assigned to items that are not originally numerical representations. The effects may include those readily observable after a medical decision. For example, an effect of a medical decision as to whether or not to send a message prompting an exercise to the smartphone of a healthy individual may be a fact of conducting or not conducting an exercise within 5 minutes of the receipt of the message.

The effects may take into consideration the costs required for a medical decision. For example, in the instances of a smartphone message as discussed, sending a message would provide merits of more easily obtaining the effects than not sending a message, but it could concurrently cause demerits of incurring a communication cost, restricting the user activities, etc. One exemplary implementation for taking such merits and demerits into consideration may be to assume, for example, that sending a first message always incurs a cost of "5" and conducting an exercise gives a reward of "100", and calculating the value of the effect as 100 (reward)−5 (cost)=95. In this manner, effects reflecting cost effectiveness can be obtained.

Feature amounts according to the embodiment include one or more attributes and/or one or more conditions of a subject. The attributes here are information items which, by nature, are not changed according to a medical decision just performed, and they include the sex, age, etc. of a subject. The conditions here are information items which, by nature, are changed according to a medical decision just performed, and they include a current blood pressure, a current blood glucose level, etc. of a subject.

A description will be given of an exemplary operation of the medical information processing apparatus 1 according to the embodiment.

FIG. 2 is a flowchart showing medical information processing conducted by the processing circuitry 11 in accordance with a medical information processing program. FIG. 3 is a diagram schematically illustrating the medical information processing shown in FIG. 2.

As shown in FIGS. 2 and 3, the processing circuitry 11 with the assignment function 111 assigns a medical decision to a patient based on a model (step 91). More specifically, the assignment is performed through the following processes.

The processing circuitry 11 includes one or more models for calculating effect evaluation values for medical decisions. Such models for calculating effect evaluation values for individual medical decisions will be called "structure models". The model or models may be adapted to calculate effect evaluation values for multiple medical decisions or to calculate an effect evaluation value for a single medical decision. The description will assume, as one example, that the models calculate effect evaluation values for multiple medical decisions. It will also be assumed that one medical decision can be detected by one structure model. It will be assumed that, by way of example, the model or models according to the embodiment include multiple structure models for handling multiple medical decisions, respectively. The processing circuitry 11 uses multiple structure models to calculate multiple effect evaluation values corresponding to the respective medical decisions. More specifically, the processing circuitry 11 applies observation data containing an effect observation value obtained from observation to each structure model so that the effect evaluation value is calculated with the structure model. The effect evaluation value may be calculated based only on observation data that is acquired from an observation conducted immediately before the processing time (processing step), or based on observation data acquired through multiple observations conducted prior to the processing time.

The processing circuitry 11 assigns an appropriate medical decision from among multiple medical decisions based on multiple effect evaluation values and according to the technique utilizing adaptive design or bandit algorithms. There are no particular restrictions on concrete algorithms for use as the bandit algorithms. In the disclosure of the embodiment, bandit algorithms mean algorithms for solving a problem of sequentially selecting appropriate medical decisions from multiple medical decisions (options) so as to maximize the sum of the effects (rewards). The bandit algorithms in the embodiment include not only narrowly-defined bandit algorithms where effects do not depend on a feature amount, but also contextual bandit algorithms where effects depend on a feature amount. The bandit algorithms in the embodiment further include reinforcement learning for solving a sequential decision-making problem where conditions vary according to the medical decisions so far. Examples of the concrete algorithms that may be used as the bandit algorithms in the embodiment include epsilon greedy, Thompson sampling, linear Thompson sampling, posterior sampling for reinforcement learning (PSRL), and Bayesian deep Q-networks (BDQN). A medical act corresponding to the medical decision is performed on a subject by a medical professional or the like, or by the subject itself. Note that the subject may receive a medical act different from the medical act corresponding to the medical decision selected by the processing circuitry 11. An effect attributable to the performed medical act is produced for the subject.

In one example, the processing circuitry 11 keeps structure models Mn for medical decisions Dn as shown in FIG. 3. Here, n is a natural number satisfying $0 \leq n \leq N$, and serves as an index to indicate the number given to the corresponding medical decision and to the corresponding structure model. The number of medical decisions and the number of structure models are each denoted by N, which is set to be one, or two or greater. In the example shown in FIG. 3, a medical decision Dn, e.g., D2, is assigned from among multiple medical decisions D1 to DN in step S1.

After step S1, the processing circuitry 11 with the observation function 112 observes the effect produced for the subject (step S2). The effect is observed in the form of numerical value or values, i.e., effect observation values. For example, if the medical decision Dn indicates "Execute a surgery", information such as a 5-year survival rate, the presence of complication incidence, and so on are acquired as the effect observation values. The effect observation values may be acquired by any methods. For example, an operator may input them via the input device 13, or a testing instrument may input its measurement values. The effect observation values may be received from one or more external computers via the communication device 14.

After step S2, the processing circuitry 11 with the accumulation function 113 accumulates the observation data in a database DB managed under the memory 12 (step S3). The observation data includes an identifier of the subject, the medical decision corresponding to the medical act performed on the subject, and the effect observation value or values from the effect produced for the subject by the medical act.

After step S3, the processing circuitry 11 with the second updating function 117 determines whether or not the structure of the model, i.e., the structure model, should be updated (step S4). The structure model may be updated at various timings or occasions, and such structure updating timings are set at a frequency lower than that for updating one or more parameters of the structure model. More specifically, the structure updating may be conducted at the timing where the observation data accumulation has reached a reference number, and/or the timing where a predetermined period of time has elapsed. Other examples of the structure updating timings include the timing where a structure model for the new medical decision is added to the models, and the timing where a structure model for the existing medical decision is discarded. As another example, the structure model may instead or additionally be updated at the timing where this updating is expected to improve the model performance.

If it is determined in step S4 that the structure model is not to be updated (step S4: NO), the processing circuitry 11 with the first updating function 116 determines whether or not one or more parameters of the structure model should be updated (step S5). The parameters of a structure model define a posterior distribution of expected values of an effect produced for the subject. The parameter or parameters may be updated at various timings or occasions, and such parameter updating timings are set at a frequency higher than that for updating the structure model. As one example, the parameter updating may be conducted at the timing where an effect is observed (the timing to acquire an effect observation value). Other examples of the parameter updating timings include the timing where the observation data accumulation has reached a reference number, and the timing where a predetermined period of time has elapsed.

If it is determined in step S5 that the parameter or parameters of the structure model is to be updated (step S5: YES), the processing circuitry 11 with the first updating function 116 updates the parameter or parameters of the structure model based on the observation data (step S6). In step S6, the processing circuitry 11 updates the parameter or parameters of the structure model while retaining the structure model. Various methods may be adopted to update parameters. For example, a parameter updating method may be determined according to the category of a decision-making problem. In the instances of one medical decision per one subject, a narrowly-defined bandit algorithm may be adopted for the updating. The narrowly-defined bandit algorithm is applicable to both the contextual bandit which assumes a context and the context-free bandit which does not assume a context. In the instances of multiple medical decisions per one subject, that is, in the instances of sequential decision making, reinforcement learning may be adopted for the updating. The reinforcement learning is applicable to both a table form and a function approximation. Note that the table form represents a case where the feature amounts (conditions) and the medical decisions (activities) are discrete values, and the function approximation represents a case where the feature amounts and the medical decisions are continuous values.

Meanwhile, if it is determined in step S4 that the structure model is to be updated (step S4: YES), the processing circuitry 11 with the second updating function 117 updates the structure model based on the observation data (step S7). Structure models may be updated in various manners. Examples of such updating manners include division and combining of structure models. Other examples of the updating manners include addition, change, deletion, etc. of a feature amount incorporated into a structure model. Change of a feature amount includes conversion between the contextual bandit and the context-free bandit. Other examples of the updating manners include addition of a structure model for the new medical decision, and discarding of a structure model for the existing medical decision. Further examples of the updating manners include change of a type of a prior distribution which the effect produced for a subject follows, and change of a network structure (hyper parameters) of a deep neural network used for the reinforcement learning.

If it is determined that the parameter or parameters of the structure model are not to be updated (step S5: NO), or if the parameter or parameters have been updated (step S6) or the structure model has been updated (step S7), the medical information processing according to the embodiment is finished. The medical information processing shown in FIGS. 2 and 3 is repeated multiple times for one model in association with a single patient or multiple patients belonging to the same patient group.

FIG. 4 is a diagram showing transitions of treatment scores of the technique according to the embodiment and the techniques according to comparative examples. The graphs given in FIG. 4 show transitions of treatment scores of the respective techniques. The vertical axis in each graph indicates a treatment score of the model according to the corresponding technique, and the horizontal axis indicates time. The treatment score is an index value that evaluates the performance of the treatment given to an individual patient. Comparative Example 1 is an example where randomized controlled trials (RCT) and machine learning are used. According to Comparative Example 1, updating is conducted at given timings such as a timing where a vast amount of observation data, e.g., on the order of thousands or tens of thousands, has been accumulated. During the accumulation of observation data, the structure and parameter of the model are not updated, and as such, the treatment score of the model is not improved. That is, a poor treatment score is shown during the accumulation of observation data. Comparative Example 2 is an example where a parameter is updated using the adaptive design or bandit algorithm technique. According to Comparative Example 2, parameter updating is conducted during the accumulation of observation data, and thus, the treatment score is improved during the accumulation of observation data. However, since the structure of the model is fixed, the degree of improvement in treatment score would be kept low. That is, although a good treatment score is shown during the accumulation of observation data, improvement in the treatment score is slow.

The method according to the embodiment conducts parameter updating during a period T41 for the observation data accumulation, while retaining the structure of the model. The method updates the structure of the model at a predetermined timing T42. Therefore, the treatment score during the accumulation of observation data is good, and also the improvement in the treatment score is fast. The method according to the embodiment allows for the repeated cyclic updating of the structure and the parameter of the model, in which, for example, the structure of the model is updated at the timing T42 where the new treatment methodology is introduced, then the parameter is updated, then the structure of the model is updated again at another timing T42 where a further new treatment methodology is introduced, and then the parameter is updated. Note that whether or not to follow the treatment methodology is one example of the medical decisions. With the method according to the embodiment, it is possible to build up an adaptive evidence-based medicine (EBM) model capable of selecting optimum medical decisions in an adaptive manner while comparing the new treatment methodology with old treatment methodologies. Together, the method according to the embodiment enables adaptive selections of optimum medical decisions for each subject, and therefore, it can realize precision medicine. Moreover, in the case of targeting models for respective subjects for the realization of precision medicine, it is possible to form the models using a smaller amount of observation data than in the cases of general-purpose models. The method according to the embodiment can also lead the way to the model formation without randomized controlled trials (RCT).

Some of the working examples according to the embodiment will be described.

Working Example 1

In Working Example 1, division of a model is conducted as the updating of the structure of the model.

FIG. 5 is a diagram schematically illustrating medical information processing according to Working Example 1. Here, steps S11 to S17 of Working Example 1 correspond to respective steps S1 to S7 shown in FIGS. 2 and 3. The description of Working Example 1 will basically omit the portions common to the medical information processing already described with reference to FIGS. 2 and 3.

It will be assumed that the parameter updating in Working Example 1 is performed by Thompson sampling, i.e., one kind of bandit algorithm. Thompson sampling is a technique for modeling parameters of the expected values of rewards in a Bayesian statistics framework, and applying a policy according to the probability matching method to the model.

The Bayesian statistics here is a statistical theory based on an interpretation that a probability changes each time information is newly acquired, and in this theory, probabilities (or a probability distribution) before and after information acquisition are subject to updating according to Bayes' theorem. The probability matching method is a method of selecting an option in each trial at the probability where the option represents the highest expected value, and options to be adopted are randomized in this technique (a stochastic policy). In the probability matching method, any methods may be employed for formulating such a "probability where the option represents the highest expected value", and one of the methods that calculates this probability from posterior probabilities according to the Bayesian approach is Thompson sampling.

It will be assumed that, as shown in FIG. 5, the initial structure models according to Working Example 1 include a structure model A for handling a medical decision of prescribing a drug A, and a structure model B for handling a medical decision of prescribing a drug B. The structure model A for the drug A calculates an effect evaluation value $Y^A$ of the drug A, and the structure model B for the drug B calculates an effect evaluation value $Y^B$ of the drug B. The effect evaluation values $Y^A$ and $Y^B$ are not limited to particular contents, but this example will assume these values to be indicative of a degree of relief of symptoms. Also, it will be assumed that the structure models according to Working Example 1 are based on the context-free bandit which does not depend on a feature amount of a subject.

In step S11, the processing circuitry 11 uses the structure model A for the drug A and the structure model B for the drug B to determine which of a medical decision A and a medical decision B should be assigned to the subject. As discussed above, a to-be-assigned medical decision is determined based on Thompson sampling in Working Example 1.

In Thompson sampling, an updated probability distribution is calculated by hypothesizing a conjugate prior distribution. It is assumed that a probability distribution of an effect (reward) produced for a subject according to a medical decision follows the Bernoulli distribution. Here, a beta distribution, which is a conjugate prior distribution of the Bernoulli distribution, is employed as a posterior distribution of expected value of the effect of the medical decision. The Bernoulli distribution refers to a discrete probability distribution where value 1 is given at probability p and value 0 is given at probability (1−p). For example, the posterior distribution of expected values of the effect of the medical decision A is represented using parameters $\alpha_A$, $\beta_A$, namely, Beta ($\alpha_A$, $\beta_A$). The parameter $\alpha_A$ indicates how many times an effect observation value "1" as the effect of the medical decision A is observed, and the parameter $\beta_A$ indicates how many times an effect observation value "0" is observed. Similarly, the posterior distribution of expected values of the effect of the medical decision B is represented using parameters $\alpha_B$, $\beta_B$, namely, Beta ($\alpha_B$, $\beta_B$).

Based on the foregoing, the effect evaluation value $Y^A$ is calculated according to equation (1) below, which takes into account an effect-followed Bernoulli distribution and a parameter $p_A$ that defines this Bernoulli distribution. Similarly, the effect evaluation value $Y^B$ is calculated according to equation (2) below, which takes into account an effect-followed Bernoulli distribution and a parameter $p_B$ that defines this Bernoulli distribution. The equation (1) is a mathematical expression of the structure model A for the medical decision A, and the equation (2) is a mathematical expression of the structure model B for the medical decision B.

$$Y^A = Bern(p_A) \tag{1}$$

$$Y^B = Bern(p_B) \tag{2}$$

According to Thompson sampling, the processing circuitry 11 determines the current option (the medical decision A or the medical decision B) in a sequential manner based on a series of effect observation values acquired before the processing time (the current step) and the selections of medical decisions. More specifically, the processing circuitry 11 randomly generates expected values $\mu_A$ and $\mu_B$ of effects of the respective options A and B from the posterior distributions Beta ($\alpha_A$, $\beta_A$) and Beta ($\alpha_B$, $\beta_B$), selects the medical decision corresponding to the highest expected value among the expected values $\mu_A$ and $\mu_B$, and assigns the selected medical decision to the subject. FIG. 5 assumes that the medical decision A is assigned.

A medical professional or the like performs a medical act corresponding to the medical decision A on the subject, whereby an associated effect is produced for the subject. In step S12, the processing circuitry 11 observes this effect as an effect observation value $Y_1^A$. In step S13, the processing circuitry 11 accumulates observation data containing the effect observation value $Y_1^A$ in the database DB. The observation data is assumed to contain at least a patient identifier and the effect observation value $Y_1^A$. Preferably, the observation data further contains any given feature amounts, e.g., the sex $x_1$ of the patient. Since Working Example 1 divides the structure model with reference to a feature amount, a feature amount expected for use in the division is added to the observation data for accumulation.

In step S16, the processing circuitry 11 updates, at a first timing, the parameter of the structure model based on the observation data. As the first timing in Working Example 1, the processing circuitry 11 updates the parameter each time an effect is observed, that is, each time an effect observation value is acquired. Specifically, upon acquisition of the effect observation value $Y_1^A$ for patient 1, the parameters $\alpha_A$ and $\beta_A$ are updated based on the observation data containing the effect observation value $Y_1^A$. The parameters $\alpha_A$ and $\beta_A$ indicate how many times "1" and "0" are observed, respectively, and therefore, these parameters are updated according to the equation (3) below. That is, the processing circuitry 11 adds "1" to the parameter $\alpha_A$ if the effect observation value $Y_1^A$ is "1", and adds "1" to the parameter $\beta_A$ if the effect observation value $Y_1^A$ is other than "1".

$$\text{if } Y^A = 1 \text{ then } \alpha_A \leftarrow \alpha_A + 1 \text{ else } \beta_A \leftarrow \beta_A + 1 \tag{3}$$

In step S17, the processing circuitry 11 updates, at a second timing, the structure model based on the observation data. Working Example 1 conducts, as the updating of the structure model, division of the structure model into structure models corresponding to values which the feature amount of the subject can take. Working Example 1 assumes that the feature amount used for the division is sex. It is possible for the feature amount "sex" to take two types of values, i.e., "male" or "female", and accordingly, the structure model that does not depend on sex is divided into a structure model for the sex "male" and a structure model for the sex "female".

As discussed above, the frequency of conducting division of the structure model is set to be lower than the frequency of updating the parameter. The division may be conducted at various timings. As one example, the processing circuitry 11 conducts division at the timing where a reference number or more sets of observation data pertaining to the feature amount used for the division have been acquired. More specifically, the processing circuitry 11 monitors the number of observation data sets accumulated in the database DB and pertaining to the feature amount used for the division, and determines whether or not the number has reached a reference number. In response to the number reaching the reference number, the structure model is divided for the feature amount based on the observation data accumulated in the database DB and pertaining to the feature amount used for the division. The reference number here may be set to any number.

FIG. 6 is a diagram showing exemplary structure models and their parameters before and after division. As shown in FIG. 6, a structure model for a medical decision i is divided into a structure model for handling the medical decision i for a male and a structure model for handling the medical decision i for a female. The symbol i represents the classification of medical decisions, and i here is either A or B. The structure model for handling the medical decision i for a male includes parameters $\alpha_{i,M}$ and $\beta_{i,M}$, and the structure model for handling the medical decision i for a female includes parameters $\alpha_{i,F}$ and $\beta_{i,F}$. In other words, the division of the structure model causes the parameter $\alpha_i$ to be divided into $\alpha_{i,M}$ and $\alpha_{i,F}$, and the parameter $\beta_i$ to be divided into $\beta_{i,M}$ and $\beta_{i,F}$. Here, $\alpha_{i,M}$ indicates how many times the effect observation value according to the medical decision i for a male patient has shown "1", and $\alpha_{i,F}$ indicates how many times the effect observation value according to the medical decision i for a female patient has shown "1". Equation (4) below holds true for the parameter $\alpha$ before and after the division. Similarly, $\beta_{i,M}$ indicates how many times the effect observation value according to the medical decision i for a male patient has shown "0", and $\beta_{i,F}$ indicates how many times the effect observation value according to the medical decision i for a female patient has shown "0". Equation (5) below holds true for the parameter p before and after the division.

$$\alpha_i = \alpha_{i,M} + \alpha_{i,F} \tag{4}$$

$$\beta_i = \beta_{i,M} + \beta_{i,F} \tag{5}$$

In step S17, the processing circuitry 11 generates post-division structure models from the pre-division structure model based on the observation data acquired before the processing time. More specifically, the acquired observation data sets are categorized into observation data for the medical Decision A pertaining to the sex "male", observation data for the medical Decision A pertaining to the sex "female", observation data for the medical Decision B pertaining to the sex "male", and observation data for the medical Decision B pertaining to the sex "female". Then, a structure model including parameters $\alpha_{A,M}$ and $\beta_{A,M}$ for handling the medical decision A for a male is generated based on the observation data for the medical Decision A pertaining to the sex "male". Also, a structure model including parameters $\alpha_{A,F}$ and $\beta_{A,F}$ for handling the medical decision A for a female is generated based on the observation data for the medical Decision A pertaining to the sex "female". Also, a structure model including parameters $\alpha_{B,M}$ and $\beta_{B,M}$ for handling the medical decision B for a male is generated based on the observation data for the medical Decision B pertaining to the sex "male". Also, a structure model including parameters $\alpha_{B,F}$ and $\beta_{B,F}$ for handling the medical decision B for a female is generated based on the observation data for the medical Decision B pertaining to the sex "female". After this division, the first updating function 116 is implemented so that the added parameters $\alpha_{i,M}$, $\alpha_{i,F}$, $\beta_{i,M}$, and $\beta_{i,F}$ will be updated.

The medical information processing according to Working Example 1 therefore comes to the end.

Working Example 1 may be modified in various ways. For example, feature amounts used for the division are not limited to sex. Other examples of the feature amounts each being capable of taking two different values include the existence of an underlying disease. Note that the feature amount capable of taking three or more discrete values or continuous values may also be adopted, and any thinkable feature amounts such as a decade of birth, weight, height, and blood pressure may be used for the division.

As another method of updating structure models, values that can be taken by a feature amount may be combined. In this case, the processing circuitry 11 combines a first number of structure models, which corresponds to the number of values that can be taken by the feature amount of a subject, into one structure model not depending on the feature amount. A working example where combining processing is conducted for the feature amount "sex" will be described briefly.

FIG. 7 is a diagram showing exemplary structure models and their parameters before and after the combining. As shown in FIG. 7, a structure model for handling the medical decision A for a male and a structure model for handling the medical decision A for a female are combined into a structure model that handles the medical decision A without distinguishing between a male and a female. Also, a structure model for handling the medical decision B for a male and a structure model for handling the medical decision B for a female are combined into a structure model that handles the medical decision B without distinguishing between a male and a female. After this combining process, the structure model for handling the medical decision A includes parameters $\alpha_A$ and $\beta_A$, and the structure model for handling the medical decision B includes parameters $\alpha_B$ and $\beta_B$.

As described above, Working Example 1 enables the updating of parameters of structure models formed based on the context-free bandit algorithm, and also the division or combining of the structure models, to be individually repeated at respective frequencies during the accumulation of observation data. Consequently, the rate and the degree of refining the medical decisions can be efficiently improved.

Working Example 2

In Working Example 2, incorporation of a new feature amount into a model is conducted as the updating of the structure of the model.

FIG. 8 is a diagram schematically illustrating medical information processing according to Working Example 2. Here, steps S21 to S27 of Working Example 2 correspond to respective steps S1 to S7 shown in FIGS. 2 and 3. The description of Working Example 2 will basically omit the portions common to the medical information processing already described with reference to FIGS. 2 and 3.

It will be assumed that, as shown in FIG. 8, the initial structure models according to Working Example 2 include a structure model A for handling a medical decision of prescribing a drug A, a structure model B for handling a medical decision of prescribing a drug B, and a structure model C for handling a medical decision of prescribing a drug C. The structure model A calculates an effect evaluation value $Y^A$ of the drug A, the structure model B calculates an effect evaluation value $Y^B$ of the drug B, and the structure model C calculates an effect evaluation value $Y^C$ of the drug C. The effect evaluation values $Y^A$, $Y^B$ and $Y^C$ are not limited to particular contents, but this example will assume these values to be indicative of a degree of relief of symptoms.

It will be assumed that Working Example 2 employs linear Thompson sampling i.e., one kind of contextual bandit algorithm, as an algorithm for determining a medical decision to be assigned. According to linear Thompson sampling, expected values and a posterior distribution of a parameter θ, used for calculating expected values of a reward, are estimated by the least-square technique, and a medical decision (option) is selected based on the probability matching method. The parameter θ takes the form of a matrix including elements of [the number of medical decisions]×[the number of feature amounts]. Here, the effect evaluation values $Y^A$, $Y^B$ and $Y_C$ can be expressed by the following equations (6), (7), and (8), respectively. The equation (6) is a mathematical expression of the structure model A for the medical decision A, the equation (7) is a mathematical expression of the structure model B for the medical decision B and the equation (8) is a mathematical expression of the structure model C for the medical decision C.

$$Y^A = \theta_1^A x_1 + \epsilon_A \tag{6}$$

$$Y^B = \theta_1^B x_1 + \epsilon_B \tag{7}$$

$$Y^C = \theta_1^C x_1 + \epsilon_C \tag{8}$$

The symbol $x_1$ indicates a first feature amount. The symbol $\theta_1^A$ indicates a parameter $\theta_1$ affecting the first feature amount of a patient A, and the symbol $\epsilon_A$ indicates a bias of the patient A. Similarly, the symbol $\theta_1^B$ indicates a parameter $\theta_1$ affecting the first feature amount of a patient B, and the symbol $\epsilon_B$ indicates a bias of the patient B. The symbol $\theta_1^C$ indicates a parameter $\theta_1$ affecting the first feature amount of a patient C, and the symbol $\epsilon_C$ indicates a bias of the patient C. The aforementioned parameter θ corresponds to $\theta_1^A$, $\theta_1^B$, and $\theta_1^C$ combined into one matrix.

In step S21, the processing circuitry 11 determines the to-be-assigned medical decision from among the medical decision A, the medical decision B, and the medical decision C, according to the algorithm of linear Thompson sampling and based on the structure model for the medical decision A, the structure model for the medical decision B, and the structure model for the medical decision C. In the case of the algorithm of linear Thompson sampling where a reward follows a normal distribution, the posterior distribution of θ is represented by a multivariate normal distribution. Accordingly, for selecting a medical decision for each patient, a random number is sampled from the multivariate normal distribution and an expected value of the reward from each option is estimated using this random number. The medical decision corresponding to the highest expected value is selected for assignment. The selected to-be-assigned medical decision is then assigned to the subject.

Supposing that a medical decision i(e) is selected and an effect $R_{i(e)}(e)$ is obtained for each patient e, where e=1, 2, . . . , or E, the least-squares estimated value $\hat{\theta}$ of θ is expressed by a ridge-regression matrix representation that uses a feature vector $x_{i(e)}(e)$, as equation (9) given below.

$$\hat{\theta} = \mathrm{argmin}_{\theta'} \left\{ \sum_{k=1}^{E} \left( R_{i(e)}(e) - (\theta')^T x_{i(e)}(e) \right)^2 + \lambda(\theta')^T \theta \right\} \quad (9)$$

$$= \left( \sum_{k=1}^{E} x_{i(e)}(e) x_{i(e)}(e) \right)^T + \frac{\sigma_0^2}{\sigma^2} I_d \right)^{-1} \sum_{k=1}^{E} x_{i(e)}(e) R_{i(e)}(e) = A^{-1} b$$

Note that $A^{-1}$ and b in the equation (9) are matrices that have substituted for the following equations (10) and (11), respectively. The symbol $I_d$ indicates a unit matrix of a d×d dimension. In Working Example 2, $A^{-1}$ and b are parameters to be updated.

$$A^{-1} = \left( \sum_{k=1}^{E} x_{i(e)}(e) x_{i(e)}(e)^T + \frac{\sigma_0^2}{\sigma^2} I_d \right)^{-1} \quad (10)$$

$$b = \sum_{k=1}^{E} x_{i(e)}(e) R_{i(e)}(e) \quad (11)$$

It is assumed that, as shown in FIG. 8, the medical decision A is assigned to patient 1 in step S21. A medical professional or the like performs a medical act corresponding to the medical decision A on patient 1, whereby an associated effect is produced for patient 1. In step S22, the processing circuitry 11 observes this effect as an effect observation value $Y_1^A$. In step S23, the processing circuitry 11 accumulates observation data containing the effect observation value $Y_1^A$ in the database DB. The observation data contains at least a patient identifier, the effect observation value. $Y_1^A$, and a given feature amount $x_1$ such as the sex $x_1$ of the patient. Since Working Example 2 adds a new feature amount $x_2$ to the structure model, the observation data for accumulation may include the feature amount $x_2$ expected to be added. FIG. 8 assumes the new feature amount $x_2$ to be an age.

In step S26, the processing circuitry 11 updates, at a first timing, the parameter of the structure model based on the observation data. In Working Example 2, the processing circuitry 11 updates the parameter each time an effect is observed, that is, each time an effect observation value is acquired. Specifically, upon acquisition of the effect observation value $Y_1^A$ for patient 1, the parameters $A^{-1}$ and b are updated based on the observation data containing the effect observation value $Y_1^A$ and the sex $x_1$, according to the following equations (12) and (13), respectively.

$$A^{-1} \leftarrow A^{-1} - \frac{A^{-1} x_{i(e)}(e) x_{i(e)}(e)^T A^{-1}}{1 + x_{i(e)}(e)^T A^{-1} x_{i(e)}(e)} \quad (12)$$

$$b \leftarrow b + x_{i(e)}(e) R_{i(e)}(e) \quad (13)$$

In step S27, the processing circuitry 11 updates, at a second timing, the structure model based on the observation data. In Working Example 2, the processing 11 adds a feature amount to the structure model, as the updating of the structure model. More specifically, the processing circuitry 11 changes the structure model including the feature amount $x_1$ ("sex") to a structure model including the feature amount $x_1$ and also the feature amount $x_2$ ("age"). The feature amount $x_2$ may be added at various timings. For example, the processing circuitry 11 may add the feature amount at the timing where accumulation of the observation data sets containing the to-be-added feature amount has reached a reference number in the database DB. The reference number is not particularly limited, and it may be any number equal to or greater than 1.

FIG. 9 is a diagram showing exemplary structure models before and after addition of the feature amount $x_2$. As shown in FIG. 9, the effect evaluation values $Y^A$, $Y^B$ and $Y^C$ after addition of the feature amount $x_2$ can be expressed by the following equations (14), (15), and (16), respectively. The equations (14), (15) and (16) are mathematical expressions of the respective structure models for the medical decisions A, B and C, each having undergone the addition of the feature amount $x_2$.

$$Y^A = \theta_1^A x_1 + \theta_2^A x_2 + \epsilon_A \quad (14)$$

$$Y^B = \theta_1^B x_1 + \theta_2^B x_2 + \epsilon_B \quad (15)$$

$$Y^C = \theta_1^C x_1 + \theta_2^C x_2 + \epsilon_C \quad (16)$$

As shown in FIG. 9, and as read from the equations (14), (15), and (16), the feature amount $x_2$ is added to the structure model for the medical decision A, the feature amount $x_2$ is added to the structure model for the medical decision B, and the feature amount $x_2$ is added to the structure model for the medical decision C. Along with the addition of the feature amount $x_2$, a parameter $\theta_2$ affecting the feature amount $x_2$ is added to the parameter $\theta$, and an element corresponding to the parameter $\theta_2$ is added to the parameters $A^{-1}$ and b. That is, the addition of the feature amount $x_2$ increases the matrix size of the parameter $\theta$ of the structure model, which also upsizes the parameters $A^{-1}$ and b. The upsized parameters $A^{-1}$ and b are not always calculable from the parameters before upsizing, and accordingly, the processing circuitry 11 calculates the upsized parameters $A^{-1}$ and b again using the observation data that has been collected up to the processing time. The updating of the structure model with the addition of the feature amount $x_2$ is conducted by applying the upsized parameters $A^{-1}$ and b to the structure model. The upsized parameters $A^{-1}$ and b will be updated as the parameters of the structure model by the first updating function 116.

The processing circuitry 11 calculates the performance of each structure model after the addition of a feature amount by utilizing the technique called off-policy evaluation in order to verify that the addition of the feature amount improves the performance. For example, the following are available as this technique: Direct Method (DM), Inverse Propensity Score (IPS), Doubly Robust (DR) (Yahoo, 2011), Replay Method (Yahoo, 2012), Counterfactual Risk Minimization (CRM) (Cornell Univ., 2015), Self-Normalized Estimator (Cornell Univ., 2015), More Robust Doubly Robust (Google DeepMind, 2018), Efficient Value Estimation (Yale Univ., Cyber Agent, 2018), and DR with Shrinkage (Cornell Univ., Netflix, Microsoft, 2019).

The processing circuitry 11 uses off-policy evaluation for each of multiple feature amount candidates intended for addition to the structure model to calculate the performance of the structure model after the addition of the feature amount, and selects the feature amount candidate that most improves the performance as the one to be added. More specifically, the processing circuitry 11 first calculates, for each of the feature amount candidates and using the off-policy evaluation, the performance of the structure model to which a feature amount candidate is added and the performance of the structure model without addition of a feature amount candidate. The processing circuitry 11 then compares, for each of the feature amount candidates, the performance of the structure model to which a feature amount candidate is added with the performance of the structure model without addition of a feature amount candidate, and selects the feature amount candidate that is expected to provide the greatest performance improvement as the feature amount to be added. The feature amount selected for addition is added to the structure model as discussed above. Note that, if there are no feature amount candidates that would provide a predetermined degree of improvement, the processing circuitry 11 may determine that the addition of a feature amount may be omitted.

The medical information processing according to Working Example 2 therefore comes to the end.

Note that Working Example 2 may also be modified in various ways. An example of such modification is a deletion or a removal of a feature amount as the updating of a structure model. In this exemplary modification, the processing circuitry 11 changes a first structure model in which multiple feature amounts are included, to a second structure model from which a given portion of the feature amounts is deleted. The deletion of one or more feature amounts may be conducted at any timing. As one example, the feature amount or amounts may be deleted at the timing where this deletion is expected to improve the performance. A working example where processing for a deletion of a feature amount is conducted will be described briefly.

FIG. 10 is a diagram showing exemplary structure models before and after deletion of a feature amount $x_2$. It will be assumed that, as shown in FIG. 10, the structure models before the deletion are structure models intended for handling respective medical decisions A, B, and C, and each including feature amounts $x_1$ and $x_2$. The feature amount $x_2$ is deleted from the original structure models for the medical decisions A, B, and C so that the structure models each including only the feature amount $x_1$ for the respective medical decisions A, B, and C are generated. The deletion of the feature amount $x_2$ reduces the matrix size of the parameter $\theta$ of the structure model, which also downsizes the parameters $A^{-1}$ and b. The downsized parameters $A^{-1}$ and b are not always calculable from the parameters before downsizing, and accordingly, the processing circuitry 11 calculates the downsized parameters $A^{-1}$ and b again using the observation data that has been collected up to the current step. A structure model from which the feature amount $x_2$ is deleted is generated by applying the downsized parameters $A^{-1}$ and b to the structure model.

As another exemplary modification, a feature amount may be changed as the updating of a structure model. In this case, the processing circuitry 11 changes a first structure model in which a first feature amount is included, to a second structure model in which a second feature amount is included in place of the first feature amount. A working example where processing for a change of a feature amount is conducted will be described briefly. This change is not limited to a particular timing, but may be set to a timing where accumulation of the observation data sets for the second feature amounts has reached a reference number or more.

FIG. 11 is a diagram showing exemplary structure models before and after replacement of a feature amount $x_1$ with a feature amount $x_2$. It will be assumed that, as shown in FIG. 11, the structure models before the change are structure models intended for handling respective medical decisions A, B, and C, and each including the feature amount $x_1$. The feature amount $x_2$ is incorporated into the original structure models for the medical decisions A, B, and C so as to replace the feature amount $x_1$, so that the structure models each including only the feature amount $x_2$ for the respective medical decisions A, B, and C are generated. The replacement of the feature amount $x_1$ with the feature amount $x_2$ does not cause a change in the matrix size of the parameter $\theta$ of the structure model, or the sizes of the parameters $A^{-1}$ and b. The processing circuitry 11 calculates the parameters $A^{-1}$ and b again for the feature amount $x_2$, using the observation data that has been collected up to the current step. A structure model in which the feature amount $x_1$ is replaced with the feature amount $x_2$ is generated by applying these recalculated parameters $A^{-1}$ and b to the structure model.

As described above, Working Example 2 enables the updating of parameters of structure models formed based on the contextual bandit algorithm, and also the addition, deletion, or replacement of feature amounts in the structure models, to be individually repeated at respective frequencies during the accumulation of observation data. Consequently, the rate and the degree of refining the medical decisions can be efficiently improved.

Others

In addition to Working Examples 1 and 2, a variety of working examples can be formulated based on the embodiments. As one example, medical decisions may be added as the updating of structure models. More specifically, in the instances where models include a first structure model for handling a first medical decision, the processing circuitry 11 adds a second structure model for handling a second medical decision to the models. A working example where processing for addition of a medical decision is conducted will be described.

FIG. 12 is a diagram showing exemplary structure models before and after addition of medical decision C. It will be assumed that, as shown in FIG. 12, the structure models before the addition are structure models intended for handling respective medical decisions A and B. Models including structure models for the respective medical decisions A, B, and C are obtained by adding a structure model for the medical decision C to the original set of structure models for the medical decisions A and B.

In one example, the addition of the structure model for the medical decision C is conducted by the following steps. First, a clinically new medical decision C is introduced. Then, observation data containing effect observation values according to the medical decision C is accumulated in the database DB in parallel with the accumulation of the observation data containing effect observation values according to the medical decisions A and B. The processing circuitry 11 monitors the number of observation data sets accumulated in the database DB and containing the effect observation values according to the medical decision C. The processing circuitry 11, upon the observation data sets reaching a reference number, generates a structure model for the medical decision C based on these observation data sets accumulated to the reference number. In another example, the processing circuitry 11 monitors the elapse of time from the start of accumulation of the observation data containing the effect observation values according to the medical decision C. The processing circuitry 11, upon the elapsed time reaching a reference time length, may generate a structure model for the medical decision C based on the observation data accumulated in the database DB and pertaining to the medical decision C.

As a further example of the updating of structure models, one or more medical decisions may be abolished. More specifically, in the instances where models include a first structure model for handling a first medical decision and a second structure model for handling a second medical decision, the processing circuitry 11 discards the first structure model or the second structure model from the models. A working example where processing for abolition of a medical decision is conducted will be described.

FIG. 13 is a diagram showing exemplary structure models before and after abolition of medical decision C. It will be assumed that, as shown in FIG. 13, the structure models before the abolition are structure models intended for handling respective medical decisions A, B, and C. Models including structure models for the respective medical decisions A and B are obtained by discarding the structure model for the medical decision C from the original set of structure models for the medical decisions A, B, and C.

The structure model for the medical decision C may be discarded at any timing or occasion, such as upon elapse of a predetermined period of time, or at the time point designated by an operator.

The description has assumed that the structure models shown in FIGS. 12 and 13 are structure models formed based on the contextual bandit algorithm and including one or more feature amounts. This is not a limitation. The disclosure herein is also applicable to structure models formed based on the context-free bandit algorithms without a feature amount.

Other examples of the updating of structure models include a manner in which the processing circuitry 11 changes a type of a prior distribution which the effect produced for a subject follows. Such change of a type may be, for example, change of a Bernoulli distribution to a normal distribution, or change of a normal distribution to a Bernoulli distribution. Still other examples of the updating of structure models include a manner in which the processing circuitry 11 changes a network structure (hyper parameters) of a deep neural network used for the reinforcement learning. The reinforcement learning employs a deep neural network as a structure model for calculating effect evaluation values. The embodiment enables, as the changes of the network structure of such a deep neural network, increasing or decreasing the number of layers in the neural network, switching between taking or not taking into account the time series, and so on.

Other examples of the parameter updating include a manner in which the processing circuitry 11 performs degradation (resetting). As one example of the degradation, the processing circuitry 11 may initialize one or more parameters of a structure model at the timing of updating the parameters. Still other examples of the parameter updating include a manner in which the processing circuitry 11 updates one or more parameters using the observation data with a limited range. Here, the observation data used for parameter updating may be restricted to, for example, observation data sets acquired during a time period starting from a predetermined length of time ago from the processing time, for the parameters of the structure model to be calculated again. As such, old observation data is excluded from the observation data to be used for the parameter updating. Therefore, for example, if there has been a change in efficacy of drugs, the observation data acquired with old drugs can be excluded for updating the parameters. Accordingly, the structure models can be endowed with improved prediction accuracy in their effect evaluation values.

The foregoing various working examples can be suitably combined. As one example, the processing circuitry 11 may conduct the division of a structure model or the combining of structure models, together with changing the type of a prior distribution as the structure updating of the structure models. The structure model division or combining and the prior distribution type change may be conducted at the same frequency or different frequencies, as long as such is performed less frequently than the updating of parameters. Also, the structure model division or combining and the prior distribution type change may be conducted at the same timing or different timings. As another example, the processing circuitry 11 may conduct the addition, deletion, or replacement of feature amounts in structure models, together with changing the network structure of a deep neural network as the structure updating of the structure models. The feature amount addition, deletion, or replacement in structure models and the network structure change of the deep neural network may be conducted at the same frequency or different frequencies, as long as such is performed less frequently than the updating of parameters. Also, the feature amount addition, deletion, or replacement in structure models and the network structure change of the deep neural network may be conducted at the same timing or different timings.

The above embodiment, etc. have assumed that the assignment function 111, the observation function 112, the accumulation function 113, the updating function 114, and the display control function 115 are mounted on one computer. However, this does not pose any limitations to the embodiment, etc. The assignment function 111, the observation function 112, the accumulation function 113, the updating function 114, and the display control function 115 may be distributed and mounted on multiple computers. In other words, the medical information processing apparatus 1 may take the form of a computer system constituted by multiple computers on which the assignment function 111, the observation function 112, the accumulation function 113, the updating function 114, and the display control function 115 are distributed and mounted. The above embodiment, etc. have also assumed that the database DB for accumulating observation data is stored in the memory 12 of the medical information processing apparatus 1. However, the embodiment, etc. are not limited to this, and the database DB may be provided in one or more computers different from the medical information processing apparatus 1. In such configurations, the medical information processing apparatus 1 may acquire observation data from the database DB via the communication device 14, or it may copy the observation data in one or more portable recording media from the database DB and acquire the observation data from the one or more portable recording media.

CONCLUSION

According to at least one embodiment described above, the medical information processing apparatus 1 includes one or more circuits as the processing circuitry 11. The one or more circuits constituting the processing circuitry 11 include the updating function 114 to update a model for calculating an effect evaluation value for a medical decision, the first updating function 116 to update a parameter of the model while retaining a structure of the model, and the second updating function 117 to update the structure of the model at a frequency lower than that for updating the parameter.

With this configuration, the structure and the parameter of the model can be updated individually at appropriate timings during the accumulation of observation data, and therefore, efficient improvement of the rate and the degree of refining medical decisions can be realized.

According to at least one embodiment described above, the rate and the degree of refining medical decisions can be efficiently improved.

The term "processor" used herein refers to, for example, a CPU or a GPU, or various types of circuitry, such as an application-specific integrated circuit (ASIC), a programmable logic device (e.g., a simple programmable logic device (SPLD), a complex programmable logic device (CPLD), or a field programmable gate array (FPGA)), and so on. The processor reads programs stored in storage circuitry and executes them to realize the intended functions. The programs may be incorporated directly in circuits of the processor, instead of being stored in the storage circuitry. According to such architecture, the processor reads the programs incorporated in its circuits and executes them to realize the functions. As another option, functions corresponding to the programs may be realized by a combination of logic circuits, instead of having the programs executed. The embodiments, etc., described herein do not limit each processor to a single circuitry-type processor. Multiple independent circuits may be combined and integrated as one processor to realize the intended functions. Furthermore, multiple components or features as given in FIG. 1 may be integrated as one processor to realize the respective functions.

While certain embodiments have been described, they have been presented by way of example only, and are not intended to limit the scope of the inventions. Indeed, the novel embodiments described herein may be embodied in a variety of other forms. Furthermore, various omissions, substitutions, and changes in the form of the embodiments may be made without departing from the spirit of the inventions. The accompanying claims and their equivalents are intended to cover such forms or modifications as would fall within the scope and spirit of the inventions.

In relation to the foregoing embodiments, etc., the following disclosures are additionally given, which set forth some of the various aspects of the inventions and alternative features thereof.

1.
A medical information processing apparatus comprising processing circuitry configured to update a model for calculating an effect evaluation value for a medical decision,
wherein the processing circuitry is configured to
update a parameter of the model while retaining a structure of the model, and
update the structure of the model at a frequency lower than that for updating the parameter.

2.
The processing circuitry may
determine the medical decision to be assigned to a subject, based on the effect evaluation value,
accumulate observation data comprising an observation value of an effect produced for the subject, and
update the model based on the observation data.

3.
The processing circuitry may, as the updating of the structure, divide the model into structure models corresponding to values which a feature amount of the subject can take.

4.
The processing circuitry may update the structure at a timing where a reference number or more sets of the observation data pertaining to the feature amount are accumulated.

5.
The model may comprise first structure models corresponding to values which a feature amount of the subject can take. The processing circuitry may, as the updating of the structure, combine the first structure models into a structure model not depending on the feature amount.

6.
The model may comprise a first structure model in which a first feature amount of the subject is included. The processing circuitry may, as the updating of the structure, change the first structure model to a second structure model in which the first feature amount and a second feature amount are included.

7.
The processing circuitry may update the structure at a timing where a reference number or more sets of the observation data pertaining to the second feature amount are accumulated.

8.
The model may comprise a first structure model in which a first feature amount of the subject is included. The processing circuitry may, as the updating of the structure, change the first structure model to a second structure model in which a second feature amount is included in place of the first feature amount.

9.
The processing circuitry may update the structure at a timing where a reference number or more sets of the observation data pertaining to the second feature amount are accumulated.

10.
The model may comprise a first structure model in which a plurality of feature amounts of are included. The processing circuitry may, as the updating of the structure, change the first structure model to a second structure model from which a predetermined portion of the feature amounts is deleted.

11.
The medical decision comprises a plurality of medical decisions including a first medical decision, and the model may comprise a first structure model for handling the first medical decision. The processing circuitry may, as the updating of the structure, add a second structure model for handling a second medical decision different from the first medical decision, to the model.

12.
The processing circuitry may add the structure model at a timing where a reference number or more sets of the observation data according to the second medical decision are accumulated.

13.
The medical decision comprises a plurality of medical decisions including a first medical decision and a second medical decision, and the model may comprise a first structure model for handling the first medical decision and a second structure model for handling the second medical decision. The processing circuitry may, as the updating of the structure, discard the first structure model or the second structure model.

14.
The processing circuitry may, as the updating of the structure, change a type of a prior distribution which the effect produced for the subject follows, the effect being attributable to a medical act corresponding to the medical decision.

15.
The processing circuitry may update the structure at a timing where a reference number or more sets of the observation data are accumulated.

16.

The processing circuitry may update the structure at a timing where a predetermined period of time elapses.

17.

The processing circuitry may update the structure at a timing where the updating is expected to improve performance of the model.

18.

The processing circuitry may update the parameter at a timing where a reference number or more sets of the observation data are accumulated or at a timing where a predetermined period of time elapses, the parameter defining a posterior distribution of expected values of the effect produced for the subject, the effect being attributable to a medical act corresponding to the medical decision.

19.

The observation value may comprise a measurement value by a testing instrument.

20.

A medical information processing method comprising an updating step of updating a model for calculating an effect evaluation value for a medical decision, wherein the updating step comprises a first updating step of updating a parameter of the model while retaining a structure of the model, and a second updating step of updating the structure of the model at a frequency lower than that for updating the parameter.

21.

A non-transitory computer-readable recording medium storing a program which causes a computer to realize an updating function for updating a model for calculating an effect evaluation value for a medical decision, wherein the updating function comprises a function for updating a parameter of the model while retaining a structure of the model, and a function for updating the structure of the model at a frequency lower than that for updating the parameter.

What is claimed is:

1. A medical information processing apparatus comprising processing circuitry including a plurality of structure models corresponding respectively to a plurality of medical decisions, each structure model of the plurality of structure models being represented by an effect-followed posterior distribution and parameters defining the effect-followed posterior distribution, wherein the processing circuitry is configured to:

calculate, for each of the plurality of medical decisions, an effect evaluation value using the corresponding effect-followed posterior distribution;

determine, from among the plurality of medical decisions, a medical decision to be assigned to a subject by executing a bandit algorithm that selects the medical decision having a highest effect evaluation value;

accumulate, in a database, observation data including an observation value of an effect produced for the subject by performing the determined medical decision;

update, in response to the accumulated observation data and as part of determining the medical decision to be assigned to the subject, the parameters of each of the plurality of structure models while retaining a structure of each of the plurality of structure models; and update the structure of each of the plurality of structure models at a frequency lower than that for updating the parameters, the updating of the structure being performed in response to a determination that an amount of the accumulated observation data satisfies a predetermined structural update condition, the updating of the structure including at least one of:

division of each of the plurality of structure models into structure models corresponding to values which a feature amount of an attribute or a condition of the subject can take;

addition, deletion, or change of the feature amount for each of the plurality of structure models;

addition of a structure model for another medical decision; or change of a type of a prior distribution representing each of the plurality of structure models.

2. The medical information processing apparatus according to claim 1, wherein the processing circuitry is further configured to update the structure at a timing where a reference number or more sets of the observation data pertaining to the feature amount are accumulated.

3. The medical information processing apparatus according to claim 1, wherein the plurality of structure models include first structure models corresponding to values which a feature amount of the subject can take, and the processing circuitry is further configured to, as the updating of the structure, combine the first structure models into a structure model not depending on the feature amount.

4. The medical information processing apparatus according to claim 1, wherein the plurality of structure models include a first structure model in which a first feature amount of the subject is included, and the processing circuitry is further configured to, as the updating of the structure, change the first structure model to a second structure model in which the first feature amount and a second feature amount are included.

5. The medical information processing apparatus according to claim 4, wherein the processing circuitry is further configured to update the structure at a timing where a reference number or more sets of the observation data pertaining to the second feature amount are accumulated.

6. The medical information processing apparatus according to claim 1, wherein the plurality of structure models include a first structure model in which a first feature amount of the subject is included, and the processing circuitry is further configured to, as the updating of the structure, change the first structure model to a second structure model in which a second feature amount is included in place of the first feature amount.

7. The medical information processing apparatus according to claim 6, wherein the processing circuitry is further configured to update the structure at a timing where a reference number or more sets of the observation data pertaining to the second feature amount are accumulated.

8. The medical information processing apparatus according to claim 1, wherein the plurality of structure models include a first structure model in which a plurality of feature amounts are included, and the processing circuitry is further configured to, as the updating of the structure, change the first structure model to a second structure model from which a predetermined portion of the feature amounts is deleted.

9. The medical information processing apparatus according to claim 1, wherein the plurality of medical decisions include a first medical decision, the plurality of structure models include a first structure model for handling the first medical decision, and the processing circuitry is further configured to, as the updating of the structure, add a second structure model for handling a second medical decision different from the first medical decision, to the model.

10. The medical information processing apparatus according to claim 9, wherein the processing circuitry is further configured to add the structure model at a timing where a reference number or more sets of the observation data according to the second medical decision are accumulated.

11. The medical information processing apparatus according to claim 1, wherein the plurality of medical decisions include a first medical decision and a second medical decision, the model comprises a first structure model for handling the first medical decision and a second structure model for handling the second medical decision, and the processing circuitry is further configured to, as the updating of the structure, discard the first structure model or the second structure model.

12. The medical information processing apparatus according to claim 1, wherein the processing circuitry is further configured to, as the updating of the structure, change a type of a prior distribution which the effect produced for the subject follows, the effect being attributable to a medical act corresponding to the medical decision.

13. The medical information processing apparatus according to claim 1, wherein the processing circuitry is further configured to update the structure at a timing where a reference number or more sets of the observation data are accumulated.

14. The medical information processing apparatus according to claim 1, wherein the processing circuitry is further configured to update the structure at a timing where a predetermined period of time elapses.

15. The medical information processing apparatus according to claim 1, wherein the processing circuitry is further configured to update the structure at a timing where the updating is expected to improve performance of the model.

16. The medical information processing apparatus according to claim 1, wherein the processing circuitry is further configured to update the parameter at a timing where a reference number or more sets of the observation data are accumulated or at a timing where a predetermined period of time elapses, the parameter defining a posterior distribution of expected values of the effect produced for the subject, and the effect being attributable to a medical act corresponding to the medical decision.

17. A medical information processing method implemented by processing circuitry including a plurality of structure models corresponding respectively to a plurality of medical decisions, each structure model of the plurality of structure models being represented by an effect-followed posterior distribution and parameters defining the effect-followed posterior distribution, the method comprising:

calculating, for each of the plurality of medical decisions, an effect evaluation value using the corresponding effect-followed posterior distribution;

determining, from among the plurality of medical decisions, a medical decision to be assigned to a subject by executing a bandit algorithm that selects the medical decision having a highest effect evaluation value;

accumulating, in a database, observation data including an observation value of an effect produced for the subject by performing the determined medical decision;

updating, in response to the accumulated observation data and as part of determining the medical decision to be assigned to the subject, the parameters of each of the plurality of structure models while retaining a structure of each of the plurality of structure models; and updating the structure of each of the plurality of structure models at a frequency lower than that for updating the parameters, the updating of the structure being performed in response to a determination that an amount of the accumulated observation data satisfies a predetermined structural update condition, the updating of the structure including at least one of:

division of each of the plurality of structure models into structure models corresponding to values which a feature amount of an attribute or a condition of the subject can take;

addition, deletion, or change of the feature amount for each of the plurality of structure models;

addition of a structure model for another medical decision; or change of a type of a prior distribution representing each of the plurality of structure models.

18. A non-transitory computer-readable recording medium storing instructions executable by processing circuitry including a plurality of structure models corresponding respectively to a plurality of medical decisions, each structure model of the plurality of structure models being represented by an effect-followed posterior distribution and parameters defining the effect-followed posterior distribution, the instructions, when executed by the processing circuitry, cause the device to:

calculate, for each of the plurality of medical decisions, an effect evaluation value using the corresponding effect-followed posterior distribution;

determine, from among the plurality of medical decisions, a medical decision to be assigned to a subject by executing a bandit algorithm that selects the medical decision having a highest effect evaluation value;

accumulate, in a database, observation data including an observation value of an effect produced for the subject by performing the determined medical decision;

update, in response to the accumulated observation data and as part of determining the medical decision to be assigned to the subject, the parameters of each of the plurality of structure models while retaining a structure of each of the plurality of structure models; and update the structure of each of the plurality of structure models at a frequency lower than that for updating the parameters, the updating of the structure being performed in response to a determination that an amount of the accumulated observation data satisfies a predetermined structural update condition, the updating of the structure including at least one of:

division of each of the plurality of structure models into structure models corresponding to values which a feature amount of an attribute or a condition of the subject can take;

addition, deletion, or change of the feature amount for each of the plurality of structure models;

addition of a structure model for another medical decision; or change of a type of a prior distribution representing each of the plurality of structure models.

19. A medical information processing apparatus comprising processing circuitry configured to:

calculate, using a model capable of calculating an effect evaluation value corresponding to a medical decision and represented by an effect-followed posterior distribution and parameters defining the effect-followed posterior distribution, the effect evaluation value corresponding to the medial decision;

determine the medical decision to be assigned to a subject by executing a bandit algorithm that selects the medical decision having a highest effect evaluation value;

acquire an effect observation value for an effect produced for the subject by applying a medical act corresponding to the determined medical decision;

accumulate, in a database, observation data including an identifier for the subject, the determined medical decision, and the acquired effect observation value; and update the model based on the accumulated observation data, wherein the processing circuitry comprises:

a first updater configured, in response to the accumulated observation data and as part of determining the medical decision to be assigned to the subject, to update the parameters of the model while retaining a structure of the model; and a second updater configured, at a frequency lower than a frequency of updating the parameters and in response to a determination that an amount of the accumulated observation data satisfies a predetermined structural update condition, to update the structure of the model by at least one of:

division of the model into a plurality of models corresponding to values which a feature amount of an attribute or a condition of the subject can take;

addition, deletion, or change of a feature amount included in the model;

addition of a model corresponding to another medical decision; or change of a type of a prior distribution representing the model.

* * * * *